US006087489A

United States Patent [19]
Dean

[11] Patent Number: 6,087,489
[45] Date of Patent: Jul. 11, 2000

[54] ANTISENSE OLIGONUCLEOTIDE MODULATION OF HUMAN THYMIDYLATE SYNTHASE EXPRESSION

[75] Inventor: Nicholas M. Dean, Encinitas, Calif.

[73] Assignee: Isis Pharmaceuticals Inc., Carlsbad, Calif.

[21] Appl. No.: 09/089,195

[22] Filed: Jun. 2, 1998

[51] Int. Cl.$^7$ .............................. C07H 21/04; C12Q 1/68
[52] U.S. Cl. ........................ 536/24.5; 536/23.1; 435/6; 435/325; 435/366
[58] Field of Search ................................ 435/6, 91.1, 375, 435/325, 366; 536/23.1, 24.34, 24.5

[56] References Cited

FOREIGN PATENT DOCUMENTS

WO 98/49287   11/1998   WIPO .

OTHER PUBLICATIONS

Aolnick et al. Oacology Res. 4:65–72, 1992.
De Moor et al. Exp. Cell Res. 243:11–21, 1998.
Crooke, Antisense Research and Application, pp. 1–50, 1998, Springer, Germany.
Branch TIBS 23:45–50, 1998.
Ferguson et al. Proced. Amer. Assoc. Cancer Res. Annual Meeting 39 p. 416, #2831, Mar., 1998.
Barker, Jr., R.H., et al. "*Plasmodium falciparum*: Effect of Chemical Structure on Efficacy and Specificity of Antisense Oligonucleotides against malaria in Vitro", Exper. Parasitology 1998, 88, 51–59.

Ju, J–F., et al. "Pharmacology/Therapeutics (Preclinical and Clinical)", Proc. Amer. Assoc. Cancer Res. 1997, 38, 478.

Kobayashi, H., et al., "Effect of Hammerhead Ribozyme against Human Thymidylate Synthase on the Cytotoxicity of Thymidylate Synthase Inhibitors", Jpn. J. Cancer Res. 1995, 86m 1014–1018.

Rappaport et al., "Antimalarial activities of oligodeoxynucleotide phosphorothioates in chloroquine–resistant *Plasmodium falciparum*", Proc. Natl. Acad. Sci., U.S.A., 1992, 89, 8577–8580.

Sartorius, C., et al., "Hybridization arrest of the cell–free translation of the malarial dihydrofolate reductase/thymidylate synthase mRNA by anti–sense oligodeoxyribonucleotides", Nucl. Acids, Res. 1991, 19, 1613–1618.

*Primary Examiner*—Robert A. Schwartzman
*Assistant Examiner*—Andrew Wang
*Attorney, Agent, or Firm*—Law Offices of Jane Massey Licata

[57] ABSTRACT

Compounds, compositions and methods are provided for modulating the expression of human thymidylate synthase. The compositions comprise antisense oligonucleotides targeted to nucleic acids encoding thymidylate synthase. Methods of using these oligonucleotides for modulation of thymidylate synthase expression and for treatment of diseases such as cancers believed to be responsive to modulation of thymidylate synthase expression are provided.

10 Claims, No Drawings

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
      (A) LENGTH: 1536 base pairs
      (B) TYPE: Nucleic Acid
      (C) STRANDEDNESS: Single
      (D) TOPOLOGY: Unknown (x) PUBLICATION INFORMATION:
      (A) AUTHORS: Takeishi,K.
          Kaneda,S.
          Ayusawa,D.
          Shimizu,K.
          Gotoh,O.
          Seno,T.
      (B) TITLE: Nucleotide sequence of a functional cDNA
          for human thymidylate synthase
      (C) JOURNAL: Nucleic Acids Res.
      (D) VOLUME: 13
      (E) ISSUE: 6
      (F) PAGES: 2035-2043
      (G) DATE: 25-MAR-1985

(xi) SEQUENCE DESCRIPTION: SEQ ID NO: 1:

```
GGGGGGGGGG GGACCACTTG GCCTGCCTCC GTCCCGCCGC GCCACTTGGC         50

CTGCCTCCGT CCCGCCGCGC CACTTCGCCT GCCTCCGTCC CCCGCCCGCC        100

GCGCCATGCC TGTGGCCGGC TCGGAGCTGC CGCGCCGGCC CTTGCCCCCC        150

GCCGCACAGG AGCGGGACGC CGAGCCGCGT CCGCCGCACG GGGAGCTGCA        200

GTACCTGGGG CAGATCCAAC ACATCCTCCG CTGCGGCGTC AGGAAGGACG        250

ACCGCACGGG CACCGGCACC CTGTCGGTAT TCGGCATGCA GGCGCGCTAC        300

AGCCTGAGAG ATGAATTCCC TCTGCTGACA ACCAAACGTG TGTTCTGGAA        350

GGGTGTTTTG GAGGAGTTGC TGTGGTTTAT CAAGGGATCC ACAAATGCTA        400

AAGAGCTGTC TTCCAAGGGA GTGAAAATCT GGGATGCCAA TGGATCCCGA        450
```

```
GACTTTTTGG ACAGCCTGGG ATTCTCCACC AGAGAAGAAG GGGACTTGGG           500

CCCAGTTTAT GGCTTCCAGT GGAGGCATTT TGGGGCAGAA TACAGAGATA           550

TGGAATCAGA TTATTCAGGA CAGGGAGTTG ACCAACTGCA AAGAGTGATT           600

GACACCATCA AAACCAACCC TGACGACAGA AGAATCATCA TGTGCGCTTG           650

GAATCCAAGA GATCTTCCTC TGATGGCGCT GCCTCCATGC CATGCCCTCT           700

GCCAGTTCTA TGTGGTGAAC AGTGAGCTGT CCTGCCAGCT GTACCAGAGA           750

TCGGGAGACA TGGGCCTCGG TGTGCCTTTC AACATCGCCA GCTACGCCCT           800

GCTCACGTAC ATGATTGCGC ACATCACGGG CCTGAAGCCA GGTGACTTTA           850

TACACACTTT GGGAGATGCA CATATTTACC TGAATCACAT CGAGCCACTG           900

AAAATTCAGC TTCAGCGAGA ACCCAGACCT TTCCCAAAGC TCAGGATTCT           950

TCGAAAAGTT GAGAAAATTG ATGACTTCAA AGCTGAAGAC TTTCAGATTG          1000

AAGGGTACAA TCCGCATCCA ACTATTAAAA TGGAAATGGC TGTTTAGGGT          1050

GCTTTCAAAG GAGCTTGAAG GATATTGTCA GTCTTTAGGG GTTGGGCTGG          1100

ATGCCGAGGT AAAAGTTCTT TTTGCTCTAA AAGAAAAAGG AACTAGGTCA          1150

AAAATCTGTC CGTGACCTAT CAGTTATTAA TTTTTAAGGA TGTTGCCACT          1200

GGCAAATGTA ACTGTGCCAG TTCTTTCCAT AATAAAAGGC TTTGAGTTAA          1250

CTCACTGAGG GTATCTGACA ATGCTGAGGT TATGAACAAA GTGAGGAGAA          1300

TGAAATGTAT GTGCTCTTAG CAAAAACATG TATGTGCATT TCAATCCCAC          1350

GTACTTATAA AGAAGGTTGG TGAATTTCAC AAGCTATTTT TGGAATATTT          1400

TTAGAATATT TTAAGAATTT CACAAGCTAT TCCCTCAAAT CTGAGGGAGC          1450

TGAGTAACAC CATCGATCAT GATGTAGAGT GTGGTTATGA ACTTTATAGT          1500

TGTTTTATAT GTTGCTATAA TAAAGAAGTG TTCTGC                         1536

(2) INFORMATION FOR SEQ ID NO: 2:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 2:

ACTCAGCTCC CTCAGATTTG                                             20

(2) INFORMATION FOR SEQ ID NO: 3:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 3:

TGGGATTGAA ATGCACATAC                                             20

(2) INFORMATION FOR SEQ ID NO: 4:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear
```

(xi) SEQUENCE DESCRIPTION: SEQ ID NO: 4:

GCCAGTGGCA ACATCCTTAA                                              20

(2) INFORMATION FOR SEQ ID NO: 5:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 5:

GCATCCAGCC CAACCCCTAA                                              20

(2) INFORMATION FOR SEQ ID NO: 6:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 6:

ACAATATCCT TCAAGCTCCT                                              20

(2) INFORMATION FOR SEQ ID NO: 7:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 7:

AAGCACCCTA AACAGCCATT                                              20

(2) INFORMATION FOR SEQ ID NO: 8:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

AAGAACCCAA ATCAGCCCTT                                              20

(2) INFORMATION FOR SEQ ID NO: 9:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 9:

CCAAGAAACC ATACCCGATT                                              20

(2) INFORMATION FOR SEQ ID NO: 10:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 10:

```
GCTAGTGGAA ACCTCCCTAA                                                    20

(2) INFORMATION FOR SEQ ID NO: 11:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION:  SEQ ID NO: 11:

ATGCGCCAAC GGTTCCTAAA                                                    20

(2) INFORMATION FOR SEQ ID NO: 12:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION:  SEQ ID NO: 12:

GGCCGGCGCG GCAGCTCCGA                                                    20

(2) INFORMATION FOR SEQ ID NO: 13:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION:  SEQ ID NO: 13:

GCAGCTCCGA GCCGGCCACA                                                    20

(2) INFORMATION FOR SEQ ID NO: 14:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION:  SEQ ID NO: 14:

GCCGGCCACA GGCATGGCGC                                                    20

(2) INFORMATION FOR SEQ ID NO: 15:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION:  SEQ ID NO: 15:

GGCATGGCGC GGCGGGCGGG                                                    20

(2) INFORMATION FOR SEQ ID NO: 16:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION:  SEQ ID NO: 16:
```

```
GGACGGAGGC AGGCGAAGTG                                                    20

(2) INFORMATION FOR SEQ ID NO: 17:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 17:

GGCCTGGCGG CGCGGGAGGG                                                    20

(2) INFORMATION FOR SEQ ID NO: 18:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 18:

ATGGGCCGGG CGGCGGGCGG                                                    20

(2) INFORMATION FOR SEQ ID NO: 19:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 19:

CGGCACGCCC ATAGGCGGCG                                                    20

(2) INFORMATION FOR SEQ ID NO: 20:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 20:

GCCTGCCGCA AGCAGGGCGC                                                    20

(2) INFORMATION FOR SEQ ID NO: 21:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 21:

CGGCACGCCC ATAGGCGGCG                                                    20

(2) INFORMATION FOR SEQ ID NO: 22:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 22:

GCCTGCCGCA AGCAGGGCGC                                                    20
```

(2) INFORMATION FOR SEQ ID NO: 23:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 23:

GCAACTCCCA GGCGGCCGCA                                      20

(2) INFORMATION FOR SEQ ID NO: 24:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 24:

TGCCGAAGCG CCACCGGCAC                                      20

(2) INFORMATION FOR SEQ ID NO: 25:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 25:

CACACTTTGG GAGATGCACA                                      20

(2) INFORMATION FOR SEQ ID NO: 26:

(i) SEQUENCE CHARACTERISTICS:
        (A) LENGTH: 25 base pairs
        (B) TYPE: Nucleic Acid
        (C) STRANDEDNESS: Single
        (D) TOPOLOGY: Linear (xi) SEQUENCE DESCRIPTION: SEQ ID NO: 26:

CTTTGAAAGC ACCCTAAACA GCCAT                              25

(2) INFORMATION FOR SEQ ID NO: 27:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 27:

TATTGGGCGC CTGGTCACCA                                      20

(2) INFORMATION FOR SEQ ID NO: 28:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 28:

CCACCTTCTT GATGTCATCA                                      20

ANTISENSE OLIGONUCLEOTIDE MODULATION OF HUMAN THYMIDYLATE SYNTHASE EXPRESSION

FIELD OF THE INVENTION

This invention relates to compositions and methods for modulating expression of the human thymidylate synthase gene, a naturally present cellular gene involved in nucleotide metabolism. This invention is also directed to methods for inhibiting hyperproliferation of cells; these methods can be used diagnostically or therapeutically. Furthermore, this invention is directed to treatment of conditions associated with expression of the human thymidylate synthase gene. This invention can also be used in combination with other therapeutic agents that target thymidylate synthase.

BACKGROUND OF THE INVENTION

Thymidylate synthase is an essential enzyme involved in nucleotide metabolism. It converts uridylate to thymidylate and provides the sole source of thymidylate for DNA biosynthesis. Since thymidylate is required for DNA biosynthesis and repair, thymidylate synthase represents an attractive target for anticancer agents. Inhibition of thymidylate synthase results in a thymineless state, which is cytotoxic to actively dividing cells. The increased growth rates of cancer cells makes them more sensitive to thymidylate synthase inhibitors than normal cells. Drugs targeting thymidylate synthase are useful against colorectal cancer, gastrointestinal, breast, head and neck, and ovarian cancers (Brandt, D. S., et al., *Oncol. Res.* 1997, 9, 403–410). The major class of drugs used to target thymidylate synthase is the fluorinated pyrimidines. Fluorinated pyrimidines, including 5-fluorouracil (5-FU) and 5-fluorodeoxyuridine (5-FUdR), compete with uridylate for binding to thymidylate synthase. In cells, 5-fluorouracil is converted to FdUMP. FdUMP takes the place of thymidylate and forms a tight binding complex with thymidylate synthase and 5,10-methylene tetrahydrofolate. 5-fluorouracil is the drug of choice for colorectal cancer. In general, response rates with 5-fluorouracil are approximately 10–15% (Brandt, D. S., et al., *Oncol. Res.* 1997, 9, 403–410).

The major problem with these types of anticancer drugs is the frequent development of drug resistance. A common mechanism by which this occurs is an increased synthesis of thymidylate synthase. Johnston, P. G., et al. (*Cancer Res.* 1995, 55, 1407–1412) demonstrated a correlation between increased thymidylate synthase gene and protein expression and a decreased responsiveness to 5-fluorouracil. Chu, E., et al. (*Proc. Natl. Acad. Sci. USA* 1991, 88, 8977–8981) demonstrated that translation of thymidylate synthase mRNA is controlled by its protein product in a negative autoregulatory manner. The binding of the thymidylate synthase protein to its mRNA prevents the translation of the mRNA. Thus drugs that bind to thymidylate synthase can result in increased expression of thymidylate synthase. Thymidylate synthase has also been associated with multidrug resistance. Chu, E., et al. (*Mol. Pharmacol.* 1991, 39, 136–143) show that cancer cell lines grown to be adriamycin-resistant developed increased expression of thymidylate synthase and showed resistance to 5-fluorouracil. Other inhibitors of thymidylate synthase have been developed in the hope that drug resistance will be less common. Several are in phase I clinical trials, with one (Tomudex, also raltitrexed; ICI D1694; N-(5-[N-(3,4-dihydro-2-methyl-4-oxoquinazolin-6-ylmethyl)-N-methylamino]-2-theonyl-L-glutamic acid)) in phase III clinical trials. However, the autoregulatory mechanism of thymidylate synthase suggests that drug resistance will not be easily overcome. In fact, resistance to Tomudex has already been seen (Johnston, P. G., et al., *J. Natl. Cancer Inst.* 1995, 87, 1558–1559).

Combinational therapy is a rational approach with thymidylate synthase inhibitors. One such relevant combination is 5-fluorouracil and leucovorin. Leucovorin is a precursor to 5,10-methylene tetrahydrofolate, and thus also binds to thymidylate synthase. Van der Wilt, C. L., et al. (*Cancer Research* 1992, 52, 4922–4928) found that in mouse cancer cell lines, leucovorin and 5-fluorouracil combination could prevent increases in thymidylate synthase expression. In a clinical trial, the combination increased the response rate to 20–30% (Rustum, Y. M., et al., *J. Clin. Oncol.* 1997, 15, 389–400).

The most common approach to targeting thymidylate synthase is the use of chemical compounds that bind to the enzyme. Although there are numerous compounds in clinical trials in an effort to achieve improved response rates compared to 5-FU or Tomudex, it is likely that resistance to these drugs will occur. Monoclonal antibodies against human thymidylate synthase are disclosed in U.S. patent application Ser. No. 07/690,841, but monoclonal antibodies typically generate an immune response against the antibody itself and thus have drawbacks for clinical use.

Oligonucleotides represent a novel approach that target the mRNA encoding thymidylate synthase, rather than the enzyme itself. Such an approach should circumvent the autoregulation of thymidylate synthase protein levels. Kobayashi, H., et al. (*Jpn. J. Cancer Res.* 1995, 86, 1014–1018) designed a ribozyme targeted to a triple tandem CUC repeat in the 5' UTR of the thymidylate synthase gene, cloned the ribozyme into a vector, and transfected the construct into a B cell lymphoblastoid cell line. They found that cell lines transfected with the ribozyme became sensitive to thymidylate synthase inhibitors. In addition, mRNA expression was reduced compared to control cells.

The use of antisense compounds represents a novel approach distinct from the use of ribozymes. An antisense oligonucleotide has been disclosed that targets the thymidylate synthase portion of the bifunctional dihydrofolate reductase-thymidylate synthase of *Plasmodium falciparum*, a causative agent of malaria [Sartorius, C., et al., *Nucl. Acids. Res.* 1991, 19, 1613–1618). Additional chemically-modified antisense oligonucleotides, including phosphorothioate, phosphodiester-phosphorothioate hybrids, and 2'-O-methyl-2'-deoxy chimeras, to the *P. falciparum* thymidylate synthase are disclosed by Barker, Jr., R. H., et al. (*Exper. Parasitology* 1998, 88, 51–59). Ju, J-F., et al. (*Proc. Amer. Assoc. Cancer Res.* 1997, 38, 478) showed that an oligonucleotide targeted to the translation start site of thymidylate synthase mRNA increased the cellular level of thymidylate synthase protein following an initial inhibition of translation. However, oligonucleotide sequences were not disclosed.

There remains a need for improved compositions and methods for modulating human thymidylate synthase gene expression.

SUMMARY OF THE INVENTION

The present invention provides oligonucleotides which are targeted to nucleic acids encoding human thymidylate synthase and are capable of modulating thymidylate synthase expression. The present invention also provides chimeric oligonucleotides targeted to nucleic acids encoding human thymidylate synthase. The oligonucleotides of the invention are believed to be useful both diagnostically and therapeutically, and are believed to be particularly useful in the methods of the present invention.

The present invention also comprises methods of modulating the expression of human thymidylate synthase using the oligonucleotides of the invention. Methods of inhibiting thymidylate synthase expression are provided; these methods are believed to be useful both therapeutically and diagnostically as a consequence of the association between thymidylate synthase expression and responsiveness to drugs designed to bind to thymidylate synthase protein. Methods of enhancing thymidylate synthase are also provided. These methods are also useful as tools, for example, for detecting and determining the role of thymidylate synthase expression in various cell functions and physiological processes and conditions and for diagnosing conditions associated with thymidylate synthase expression.

The present invention also comprises methods of inhibiting hyperproliferation of cells using oligonucleotides of the invention and methods for protecting a subset of cells from chemotherapeutic agents. These methods are believed to be useful, for example, in diagnosing thymidylate synthase-associated responsiveness to antifolate drugs. Methods of treating abnormal proliferative conditions associated with thymidylate synthase are also provided. These methods include the use of combinational therapies for improving the efficacy of current drugs. These methods employ the oligonucleotides of the invention. These methods are believed to be useful both therapeutically and as clinical research and diagnostic tools.

DETAILED DESCRIPTION OF THE INVENTION

Thymidylate synthase represents an attractive target for antineoplastic therapy. It is an essential enzyme in DNA biosynthesis and is expressed in actively dividing cells. Many anti-cancer approaches seek to exploit the rapid division of cancer cells, and one such approach is through the use of thymidylate synthase inhibitors, such as 5-fluorouracil and Tomudex. Such drugs covalently bind to thymidylate synthase and prevent the enzyme from interacting with its natural substrate. This results in a thymineless state where DNA can not be synthesized. Thymidylate synthase inhibitors are therefore believed to have a broad range of activity against a wide variety of cancers. In particular, 5-fluorouracil has demonstrated clinical efficiency for many tumors, including gastrointestinal, breast, head, neck, and ovarian (B3 randt, D. S., et al., *Oncol. Res.* 1997, 9, 403–410). A problem with the current state of thymidylate synthase inhibitors is the development of drug resistance. The most common mechanism by which this occurs is increased translation of the thymidylate synthase gene. A negative feedback loop exists between the protein and the mRNA. By targeting the protein, conventional thymidylate synthase inhibitors may be signaling the cell to increase thymidylate synthase expression in an effort to increase thymidylate synthase protein levels. Although conventional thymidylate synthase inhibitors have been used in combination with other drugs including folate analogues, the response rate was not improved significantly. It is believed that targeting the thymidylate synthase mRNA can result in more effective inhibition of the thymidylate synthase enzyme. Such targeting can also be in combination with drugs that target the protein.

The present invention employs antisense compounds, particularly oligonucleotides, for use in modulating the function of nucleic acid molecules encoding thymidylate synthase, ultimately modulating the amount of thymidylate synthase produced. This is accomplished by providing oligonucleotides which specifically hybridize with nucleic acids, preferably mRNA, encoding thymidylate synthase.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding thymidylate synthase; in other words, a thymidylate synthase gene or mRNA expressed from a thymidylate synthase gene. Thymidylate synthase mRNA is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding thymidylate synthase, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include. the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of thymidylate synthase expression. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application.

The oligonucleotides of this invention can be used in diagnostics, therapeutics, prophylaxis, and as research reagents and in kits. Since the oligonucleotides of this invention hybridize to nucleic acids encoding thymidylate synthase, sandwich, colorimetric and other assays can easily be constructed to exploit this fact. Provision of means for detecting hybridization of oligonucleotide with a thymidylate synthase gene or mRNA can routinely be accomplished. Such provision may include enzyme conjugation, radiolabelling or any other suitable detection systems. Kits for detecting the presence or absence of thymidylate synthase may also be prepared.

The present invention is also suitable for diagnosing abnormal proliferative states in tissue or other samples from patients suspected of having a hyperproliferative disease such as cancer. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal. Similarly, the present invention can be used to distinguish thymidylate synthase-associated tumors from tumors having other etiologies, in order that an efficacious treatment regimen can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thiono-alkylphosphonates, thionoalkylphosphotriesters, and borano-phosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262. Further teaching of PNA compounds can be found in Nielsen et al. (*Science*, 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl, O-alkyl-O-alkyl, O—, S—, or N-alkenyl, or O—, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m CH_3$, O($CH_2$)$_n$O$CH_3$, O($CH_2$)$_2$ON($CH_3$)$_2$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, ONO$_2$, NO$_2$, N$_3$, NH$_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta* 1995, 78, 486–504) i.e., an alkoxyalkoxy group.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, International Edition* 1991, 30, 613–722), and those disclosed by Sanghvi, Y. S., Chapter 15, *Antisense Research and Applications* 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylaminocarbonyl-oxycholesterol moiety (Crooke et al., *J. Pharmacol. Exp. Ther.* 1996, 277, 923–937).

Representative United States patents that teach the preparation of such oligonucleotide conjugates include, but are not limited to, U.S. Pat. Nos.: 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endo-nuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., 2'-fluoro- or 2'-O-methoxyethyl-substituted). Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl- substituted), or vice-versa. In one embodiment, the oligonucleotides of the present invention contain a 2'-O-methoxyethyl (2'-O—CH$_2$CH$_2$OCH$_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH$_2$CH$_2$OCH$_3$) modification. oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta* 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included. Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a.

1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654).

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. Preferred are chemotherapeutic agents which are direct or indirect inhibitors of thymidylate synthase. These include MTX, Tomudex and fluorinated pyrimidines such as 5-FU and 5-FUdR. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

Thus, in the context of this invention, by "therapeutically effective amount" is meant the amount of the compound which is required to have a therapeutic effect on the treated individual. This amount, which will be apparent to the skilled artisan, will depend upon the age and weight of the individual, the type of disease to be treated, perhaps even the gender of the individual, and other factors which are routinely taken into consideration when designing a drug treatment. A therapeutic effect is assessed in the individual by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor.

The following examples illustrate the present invention and are not intended to limit the same.

EXAMPLES

EXAMPLE 1
Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy µ-cyanoethyldiisopropyl-phosphoramidites (Chemgenes, Needham, Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al. (*J. Med. Chem.* 1993, 36, 831–841). Briefly, the protected nucleoside $N^6$-benzoyl-2'-deoxy-2'-fluoroadenosine was synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9β-D-arabinofuranosyladenine was selectively protected in moderate yield as the 3', 5'-ditetrahydropyranyl (THP) intermediate. Deprotection of the THP and $N^6$-benzoyl groups was accomplished using standard methodologies and standard methods were used to obtain the 5'-dimethoxytrityl-(DMT) and 5'-DMT-3'-phosphoramidite intermediates.

The synthesis of 2'-deoxy-2'-fluoroguanosine was accomplished using tetraisopropyldisiloxanyl (TPDS) protected 9β-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a known procedure in which 2, 2'-anhydro-1-β-D-arabinofuranosyluracil was treated with 70% hydrogen fluoride-pyridine. Standard procedures were used to obtain the 5'-DMT and 5'-DMT-3'phosphoramidites.

2'-deoxy-2'-fluorocytidine was synthesized via amination of 2'-deoxy-2'-fluorouridine, followed by selective protection to give N[4]-benzoyl-2'-deoxy-2'-fluorocytidine. Standard procedures were used to obtain the 5'-DMT and 5'-DMT-3' phosphoramidites.

2'-(2-methoxyethyl)-modified amidites are synthesized according to Martin, P. (*Helv. Chim. Acta* 1995, 78, 486–506). For ease of synthesis, the last nucleotide was a deoxynucleotide. 2'-O—CH$_2$CH$_2$OCH$_3$-cytosines may be 5-methyl cytosines.

Synthesis of 5-Methyl cytosine monomers:

2,2'-Anhydro[1-(β-D-arabinofuranosyl)-5-methyluridine]:

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxy-trityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyl-uridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to -5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N[4]-Benzoyl-2'-O-methoxyethyl-5'-O-dimethoxytrityl-5-methyl-cytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N⁴-Benzoyl-2'-O-methoxyethyl-5'-O-dimethoxytrityl-5-methylcytidine-3'-amidite:

N⁴-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., *Nucl. Acids Res.* 1993, 21, 3197–3203) using commercially available phosphoramidites (Glen Research, Sterling Va. or ChemGenes, Needham Mass.).

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages were synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (*Science* 1991, 254, 1497–1500).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by ³¹P nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

EXAMPLE 2

Human Thymidylate Synthase Oligonucleotide Sequences

Antisense oligonucleotides were designed to target human thymidylate synthase. Target sequence data are from the thymidylate synthase cDNA sequence published by Takeishi, K., et al. (*Nucleic Acids Res.* 1985, 13, 2035–2043); Genbank accession number X02308, provided herein as SEQ ID NO: 1. Oligonucleotides were synthesized primarily as chimeric oligonucleotides having a centered deoxy gap of eight nucleotides flanked by 2'-O-methoxyethyl regions. All 2'-O-methoxyethyl cytidines were made as 5-methylcytidines.

Oligonucleotides were designed and synthesized to target the stop codon and 3'-untranslated region (3'-UTR), shown in Table 1, or to the start codon and surrounding region, shown in Table 2.

HeLa, human cervical carcinoma cells (obtained from American Type Culture Collection) were cultured in Dulbecco's modified Eagle's medium (DMEM), 10% fetal bovine serum, and penicillin (50 units/ml) /streptomycin (50 mg/ml). All culture reagents were obtained from Canadian Life Technologies (GIBCO BRL, Burlington, ON, Canada). HeLa cells were plated at a starting cell number of between 0.6 to 1×10⁵ cells per 25-cm² tissue culture flask. Cells were treated with phosphorothioate oligonucleotides at 25 nM or 50 nM for six hours in the presence of 3 mg/ml LIPOFECTAMINE™ (GIBCO BRL), a 3:1 (w/w) liposome formulation of the polycationic lipid 2,3-dioleyloxy-N-[2 (sperminecarboxamido)ethyl]-N,N-dimethyl-1-propanaminium trifluoroacetate (DOSPA) and the neutral lipid dioleoyl phosphatidylethanolamine (DOPE), in serum-free DMEM medium, washed and allowed to recover for an additional 4 days. In cells treated with cytotoxic agent, exposure was initiated 24 hours after the removal of LIPOFECTAMINE™/oligonucleotide, by addition of 0.2 volume of growth medium containing the agent at six times the final concentration. At the time of addition of drug, and after four days of incubation, cell numbers were determined from replicate flasks by enumerating with a particle counter (Coulter Electronics, Hialeah, Fla.). The proliferation of drug-treated cells (fold-increase in cell number) was calculated as a percentage of that of the control cells.

Results are shown in Table 3. Oligonucleotides 13783 (SEQ ID NO: 4), 13784 (SEQ ID NO: 5), 13786 (SEQ ID NO: 7) and 13787 (SEQ ID NO: 12) gave about 40% inhibition of cell proliferation, where about is plus or minus 5%. Oligonucleotide 13784 (SEQ ID NO: 5) gave better than 50% inhibition.

TABLE 1

Nucleotide Sequences of Human Thymidylate Synthase Oligonucleotides

| ISIS NO: | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 13781 | ACTCAGCTCCCTCAGATTTG | 2 | 1436–1455 | 3'-UTR |
| 13782 | TGGGATTGAAATGCACATAC | 3 | 1330–1349 | 3'-UTR |
| 13783 | GCCAGTGGCAACATCCTTAA | 4 | 1184–1203 | 3'-UTR |
| 13784 | GCATCCAGCCCAACCCCTAA | 5 | 1085–1104 | 3'-UTR |

TABLE 1-continued

Nucleotide Sequences of Human Thymidylate Synthase Oligonucleotides

| ISIS NO: | NUCLEOTIDE SEQUENCE (5' -> 3') | SEQ ID NO: | TARGET GENE NUCLEOTIDE CO-ORDINATES[1] | GENE TARGET REGION |
| --- | --- | --- | --- | --- |
| 13785 | ACAATATCCTTCAAGCTCCT | 6 | 1059–1078 | 3'-UTR |
| 13786 | AAGCACCCTAAACAGCCATT | 7 | 1035–1054 | STOP |
| 16029 | AAGAACCCAAATCAGCCCTT | 8 | 13786 mismatch | |
| 16030 | CCAAGAAACCATACCCGATT | 9 | 13786 scrambled | |
| 16031 | GCTAGTGGAAACCTCCCTAA | 10 | 13783 mismatch | |
| 16032 | ATGCGCAACGGTTCCTAAA | 11 | 13783 scrambled | |

[1]Emboldened residues are 2'-methoxyethoxy residues (others are 2'-deoxy-). All 2'-methoxyethoxy cytidines are 5-methylcytidines; all linkages are phosphorothioate linkages.
[2]Co-ordinates from Genbank Accession No. X02308, locus name "HSTSYN1", SEQ ID NO: 1.

TABLE 2

Nucleotide Sequences of Start Codon-directed Human Thymidylate Synthase Oligonucleotides

| ISIS NO: | NUCLEOTIDE SEQUENCE (5' -> 3') | SEQ ID NO: | TARGET GENE NUCLEOTIDE CO-ORDINATES[1] | GENE TARGET REGION |
| --- | --- | --- | --- | --- |
| 13787 | GGCCGGCGCGGCAGCTCCGA | 12 | 0121–0140 | coding |
| 13788 | GGCCGGCGCGGCAGCTCCGA | 12 | " | coding |
| 13789 | GCAGCTCCGAGCCGGCCACA | 13 | 0111–0130 | coding |
| 13790 | GCAGCTCCGAGCCGGCCACA | 13 | " | coding |
| 13791 | GCCGGCCACAGGCATGGCGC | 14 | 0101–0120 | AUG |
| 13792 | GCCGGCCACAGGCATGGCGC | 14 | " | AUG |
| 13793 | GGCATGGCGCGGCGGGCGGG | 15 | 0091–0110 | AUG |
| 13794 | GGCATGGCGCGGCGGGCGGG | 15 | " | AUG |
| 13795 | GGACGGAGGCAGGCGAAGTG | 16 | 0071–0090 | 5'-UTR |
| 13796 | GGACGGAGGCAGGCGAAGTG | 16 | " | 5'-UTR |
| 16021 | GGCCTGGCGGCGCGGGAGGG | 17 | 13793 mismatch | |
| 16022 | ATGGGCCGGGCGGCGGGCGG | 18 | 13793 scrambled | |
| 16023 | CGGCACGCCCATAGGCGGCG | 19 | 13792 scrambled | |
| 16024 | GCCTGCCGCAAGCAGGGCGC | 20 | 13792 mismatch | |
| 16025 | CGGCACGCCCATAGGCGGCG | 21 | 13791 scrambled | |
| 16026 | GCCTGCCGCAAGCAGGGCGC | 22 | 13791 mismatch | |
| 16027 | GCAACTCCCAGGCGGCCGCA | 23 | 13790 mismatch | |
| 16028 | TGCCGAAGCGCCACCGGCAC | 24 | 13790 scrambled | |

[1]Emboldened residues are 2'-methoxyethoxy residues (others are 2'-deoxy). All 2'-methoxyethoxy cytidines are 5-methylcytidines; all linkages are phosphorothioate linkages.
[2]Co-ordinates from Genbank Accession No. X02308, locus name "HSTSYN1."

TABLE 3

Inhibition of HeLa Cell Proliferation by Phosphorothioate
Oligonucleotides Targeted to Human Thymidylate Synthase

| ISIS No: | SEQ ID NO: | GENE TARGET REGION | OLIGO CONC. (nM) | % CELL GROWTH | % INHIB'N OF CELL GROWTH |
|---|---|---|---|---|---|
| LIPO-FECTAMINE ™ only | — | — | — | 100.0% | 0.0% |
| 13783 | 4 | 3'-UTR | 25 | 82.5% | 17.5% |
| " | " | " | 50 | 57.2% | 42.8% |
| 13784 | 5 | 3'-UTR | 25 | 47.2% | 52.8% |
| " | " | " | 50 | 44.2% | 55.8% |
| 13785 | 6 | 3'-UTR | 50 | 77.7% | 22.3% |
| 13786 | 7 | STOP | 50 | 61.4% | 38.6% |
| 13787 | 12 | ORF | 50 | 59.8% | 40.2% |
| 13791 | 14 | AUG | 50 | 128.0% | — |
| 16030 | 9 | scrambled | 50 | 87.7% | 12.3% |
| 16032 | 11 | scrambled | 25 | 88.5% | 11.5% |
| " | " | " | 50 | 83.2% | 16.8% |

EXAMPLE 3

Effect on HeLa Cell Proliferation of Antisense Oligonucleotides Used in Combination with Tomudex.

Antisense oligonucleotides were tested for an ability to enhance the anti-proliferative effect of Tomudex on HeLa cells. Proliferation assays were performed as described in Example 2 except that Tomudex was added 24 hours after transfection.

Dose response curves were plotted based on Tomudex concentrations of 1.5, 2.0, 2.5, 3.0, 4.0 and 5.0 nM. Both an $IC_{50}$ and an $IC_{90}$ value were derived from the dose response curve.

Results are shown in Table 4. Oligonucleotides 13783 (SEQ ID NO: 4), 13784 (SEQ ID NO: 5), 13785 (SEQ ID NO: 6), 13786 (SEQ ID NO: 7) and 13787 (SEQ ID NO: 12) decreased the IC values by 14% or greater. Oligonucleotides 13783 (SEQ ID NO: 4), 13784 (SEQ ID NO: 5) and 13785 (SEQ ID NO: 6) decreased the IC values by about 22% or greater.

TABLE 4

Inhibition of Proliferation of HeLa Cells by Phosphorothioate
Oligonucleotides in Combination with Tomudex

| ISIS No: | SEQ ID NO: | GENE TARGET REGION | OLIGO CONC. (nm) | relative $IC_{50}$ value[1] | relative $IC_{90}$ value[1] |
|---|---|---|---|---|---|
| 13783 | 4 | 3'-UTR | 50 | 63.0% | 67.2% |
| 13784 | 5 | 3'-UTR | 25 | 76.1% | 77.5% |
| " | " | " | 50 | 62.0% | 75.1% |
| 13785 | 6 | 3'-UTR | 50 | 59.8% | 69.8% |
| 13786 | 7 | STOP | 50 | 73.9% | 81.4% |
| 13787 | 12 | ORF | 50 | 85.9% | 78.4% |
| 13791 | 14 | AUG | 50 | 98.9% | 85.2% |
| 16032 | 11 | scrambled | 50 | 100.0% | 100.0% |

[1]Expressed as a percentage of oligonucleotide 16032 (SEQ ID NO: 11) control

EXAMPLE 4

Effect of ISIS 16783 on Thymidylate Synthase Levels

The effect of oligonucleotide 16783 on thymidylate synthase mRNA levels and protein levels over a four day period was determined.

RT-PCR assay

Thymidylate synthase mRNA levels were measured using Reverse Transcriptase Polymerase Chain Reaction (RT-PCR). Total RNA was isolated from cells using TRIZOL® (GIBCO BRL, Burlington, ON, Canada), a mono-phasic solution of phenol and guanidine isothiocyanate. cDNA was reverse transcribed from total RNA using Moloney Murine Leukemia Virus reverse transcriptase (MMLV-RT, GIBCO BRL) in 50 mM Tris-HCl (pH 8.3), 75 mM KCl, 3mM $MgCl_2$, 1 mM mixed dNTPs, 100 pmol random primers and 10 mM dithiothreitol at 37° C. for one hour. The enzyme was inactivated at 95° C. for 5 minutes. The cDNAs were amplified in a PCR reaction using 1.25 U of Taq DNA Polymerase (GIBCO BRL) in 50 ml of 20 mM Tris-HCl (pH 8.4), 50 mM KCl, 0.2 mM mixed dNTPs, 2 mM $MgCl_2$, and 50 pmol of thymidylate synthase (TS) and glycerol aldehyde phosphate dehydrogenase (GAPDH) specific primers.

| | | |
|---|---|---|
| TS forward | 5'-CACACTTTGGGAGATGCACA-3' | SEQ ID NO: 25 |
| TS reverse | 5'-CTTTGAAAGCACCCTAAACAGCCAT-3' | SEQ ID NO: 26 |
| GAPDH forward | 5'-TATTGGGCGCCTGGTCACCA-3' | SEQ ID NO: 27 |
| GAPDH reverse | 5'-CCACCTTCTTGATGTCATCA-3' | SEQ ID NO: 28 |

PCR reactions consisted of twenty-four to twenty-seven cycles (94° C., 45 seconds; 55° C., 30 seconds; 72° C., 90 seconds) PCR products were separated on a 1.2% agarose gel and transferred to HYBOND™-N (Amersham, Canada, Ltd., Oakville, ON, Canada), a neutral nylon membrane. The blots were probed with a [$\alpha$-$^{32}$P] dCTP random primer-labeled thymidylate synthase cDNA probe or G3PDH probe. Standard methods for radio-labeling nucleic acid fragments are readily available, see for example, Maniatis, T., et al., Molecular Cloning: A Laboratory Manual 1989, chapter 10. Thymidylate synthase transcripts were examined and quantified with a PhosphorImager™ (Molecular Dynamics, Sunnyvale, Calif.).

Thymidylate Synthase Protein Assay

Thymidylate synthase protein levels were measured by binding to [6-$^3$H]5-FdUMP (Moravek Biochemicals, Brea, Calif.). After cells were treated with the antisense oligonucleotide, ISIS 13783 (SEQ ID NO: 4), cells were harvested and resuspended in 100 mM $KH_2PO_4$ (pH 7.4). The cell pellet was then subjected to a freeze-thaw cycle, followed by sonication. Total protein concentration was determined by Coomassie Blue staining (BioRad, Hercules, Calif.). Reactions were carried out with 50 $\mu$g total protein, 75 $\mu$M methylene tetrahydrofolate, 100 mM mercaptoethanol, 50 mM $KH_2PO_4$ (pH 7.4), and 15 nM (6-$^3$H]5-FdUMP. The reaction proceeded for 30 minutes at 37° C., then stopped by the addition of five volumes of albumin-coated activated charcoal. After ten minutes, the reaction was centrifuged twice (3000×g, 30 minutes, 22° C.). Aliquots of the supernatant were removed for scintillation counting.

Results are shown in Table 5. Oligonucleotide 13783 (SEQ ID NO: 4) decreased both mRNA and protein levels.

TABLE 5

Time-course of ISIS 13783 on Thymidylate Synthase Levels

| ISIS No: | SEQ ID NO: | GENE TARGET REGION | TIME (HOURS) | RELATIVE mRNA LEVEL[1] | RELATIVE PROTEIN LEVEL[1] |
|---|---|---|---|---|---|
| 13783 | 4 | 3'-UTR | 24 | 30% | 24% |
| " | " | " | 48 | 57% | 42% |
| " | " | " | 96 | 64% | 77% |

[1]Expressed relative to Oligonucleotide 16032 (SEQ ID NO: 11)

EXAMPLE 5
Effect of ISIS 16783 in Combination with Thymidylate Synthase Targeted Drugs Oligonucleotide 16783 (SEQ ID NO: 4) was tested in combination with thymidylate synthase targeted drugs. These include Tomudex, methotrexate, 5-fluorouracil (5-FU), and 5-fluorodeoxyuridine (5-FUdR, the active metabolite of 5-FU). Cell proliferation assays were performed as described in Example 3, with the appropriate drug substituted for Tomudex as listed. Concentrations of 5-fluorouracil used were 1, 2, 4, 8, and 10 nM. Concentrations of 5-FUdR used were 0.5, 1, 2, 4, and 8 nM. Concentrations of Tomudex used were 1.5, 2.0, 2.5, 3.0, 4.0, and 5.0 nM. Concentrations of methotrexate used were 10, 15, 20, 25, 30, and 40 nM. $IC_{50}$ and $IC_{90}$, if present, values were derived from the dose response curves. Oligonucleotide 16032 (SEQ ID NO: 11) was used as a control.

$IC_{50}$ and $IC_{90}$, values are expressed as a percentage of the values obtained using oligonucleotide 16032. With the drugs tested, oligonucleotide 16783 (SEQ ID NO: 4) reduced the IC values. Values are relative to values obtained with ISIS 13783 alone, without added cytotoxic drug. Thus, the enhancement of sensitivity to these drugs is separate from and in addition to the cytostatic effect of ISIS 13783 alone. ISIS 13783 did not sensitize HeLa cells to the cytotoxic drugs cisplatin or chlorambucil, neither of which is known to target the thymidylate synthase complex.

TABLE 6

Effect of Combinational Therapy of ISIS 16783 with anti-Thymidylate Synthase Drugs on HeLa Cell Proliferation

| ISIS No: | SEQ ID NO: | DRUG | OLIGO CONC. (nM) | RELATIVE $IC_{50}$ VALUE | RELATIVE $IC_{90}$ VALUE |
|---|---|---|---|---|---|
| 13783 | 4 | Tomudex | 50 | 56.0% | 69.3% |
| " | " | MTX | 50 | 85% | |
| " | " | 5-FU | 50 | 67% | 39% |
| " | " | 5-FUdR | 50 | 28.3% | 34.3% |

EXAMPLE 6
Enhancement of Thymidylate Synthase Expression

MCF-7, human breast adenocarcinoma (obtained from American Type Culture Collection), and HeLa, human cervical carcinoma cells were cultured in Dulbecco's modified Eagle's medium (DMEM), 10% fetal bovine serum, 2 mM glutamine, 10 mM Hepes (pH 7.4) and 0.1% gentamycin. All culture reagents were obtained from Canadian Life Technologies (GIBCO, Burlington, ON, Canada).

MCF-7 cells were grown to approximately $1.5 \times 10^6$ cells in 100×15 mm tissue culture plates. Cells were treated with phosphorothioate oligonucleotides at 0.5 µM or 1 µM for six hours in the presence of 2 µg/ml LIPOFECTAMINE™, in Opti-DMEM medium, washed and allowed to recover for an additional 48 hours.

Run-on Transcription

Relative transcription rates were determined by a nuclear run-on assay. Nuclei were isolated forty-eight hours after transfection of cells with oligonucleotides. All steps were carried out at 4° C. Cells were rinsed twice with ice-cold phosphate buffered saline (PBS), scraped off using a rubber policeman, pelleted (5 minutes, 500×g), and lysed by incubating 5 minutes at 4° C. in lysis buffer (10 mM Tris-Cl, pH 7.4, 10 mM NaCl, 3 mM $MgCl_2$, 0.5% NP-40). Nuclei were pelleted by centrifugation (5 minutes, 500×g) and resuspended in lysis buffer, pelleted again by centrifugation, and final resuspension in 200 ml of storage buffer (40% glycerol, 5 mM $MgCl_2$, 50 mM Tris-HCl, pH 8.0, 0.1 mM EDTA).

RNA elongation reactions were performed for 30 minutes at 30° C. using $2 \times 10^7$ nuclei. Reactions were composed of 200 µl storage buffer plus 200 µl of sterile 2× reaction buffer (10 mM Tris-HCl, pH 8.0, 5 mM $MgCl_2$, 0.3 M KCl, 1 mM ATP, 1 mM CTP, 1 mM GTP, 5 mM dithiothreitol, and 2 µl [α-$^{32}$P]UTP or [α-$^{32}$P] CTP (~3000 Ci/mmol, 10 mCi/ml) (Amersham Canada Ltd., Oakville, ON, Canada). Nucleotides and dithiothreitol were added immediately prior to use. The reaction took place on a shaking platform to facilitate mixing. After the reaction was complete, 600 ml of RNase-free DNase I (Promega Corp, Madison, Wis.) in 0.5 M NaCl, 50 mM $MgCl_2$, 2 mM $CaCl_2$, 10 mM Tris-HCl, pH 7.4 was added. RNA was isolated using TRIZOLO® (GIBCO BRL) and dissolved in Church hybridization buffer (1 mM EDTA, 0.5 mM $NaHPO_4$, pH 7.2, 7% sodium lauryl sulfate (SLS) to a final concentration of $4 \times 10^6$ cpm/ml.

Thymidylate gene transcription was measured by hybridization of radiolabeled TS RNA to target DNA (a 1.9 kb XhoI fragment from pcHTS-1 (Takeishi, K., et al., *Nucleic Acids Res.* 1985 13, 2035–2043) immobilized on nitrocellulose filters. cDNAs for GAPDH and 18s rRNA were also added to filters as a control. Filters were prehybridized in Church buffer for 20 minutes at 65° C. The buffer was removed and 2 ml of the run-on transcription reaction was added. The filters were hybridized for 48 hours at 65° C., washed twice at 65° C. in posthybridization buffer (40 mM $Na_2HPO_4$, 1% SDS) for 20 minutes each. Posthybridization buffer was removed and RNase A was added for 30 minutes at 37° C. After a final wash in posthybridization buffer, 10 minutes at 37° C., filters were blotted dry and quantitated with a PhosphorImager (Molecular Dynamics, Sunnyvale, Calif.). Relative transcription rates were expressed at a ratio of thymidylate synthase signal to GAPDH or 18s rRNA signal.

Results are shown in Table 7. ISIS 13786, targeted to the stop codon, did not have a significant or dose-dependent effect on thymidylate synthase protein expression. Oligonucleotides 13790 (SEQ ID NO: 13) and 13792 (SEQ ID NO: 14) increased the transcription rate over 60% at 0.5 mM and over 180% at 1.0 µM. Both 13790 and 13792 enhanced thymidylate synthase expression in a dose-dependent manner. Oligonucleotide 13792 (SEQ ID NO: 14) increased the transcription rate over 90% at 0.5 µM and over 260% at 1.0 µM.

TABLE 7

Enhancement of Thymidylate Synthase Expression with Antisense Phosphorothioate Oligonucleotides

| ISIS NO: | SEQ ID NO: | GENE TARGET REGION | OLIGO CONC. (mM) | RELATIVE TRANSCRIPTION RATE |
|---|---|---|---|---|
| LIPOFECTANINE ™ only | — | — | — | 100% |
| 13786 | 7 | STOP | 0.5 | 126% |
| " | " | " | 1.0 | 126% |
| 13790 | 12 | ORF | 0.5 | 164% |
| " | " | " | 1.0 | 283% |
| 13792 | 14 | AUG | 0.5 | 192% |
| " | " | " | 1.0 | 362% |
| 16023 | 19 | scrambled | 0.5 | 107% |
| " | " | " | 1.0 | 95% |
| 16028 | 24 | scrambled | 0.5 | 107% |
| " | " | " | 1.0 | 95% |

What is claimed is:

1. An antisense oligonucleotide 8 to 30 nucleotides in length comprising a nucleotide sequence complementary to a nucleic acid molecule encoding human thymidylate synthase, wherein said oligonucleotide is complementary to the 3' untranslated region of said nucleic acid molecule and inhibits the expression of said human thymidylate synthase.

2. The oligonucleotide of claim 1 comprising SEQ ID NO: 2, 3, 4, 5, or 6.

3. The oligonucleotide of claim 1 comprising SEQ ID NO: 4.

4. The oligonucleotide of claim 1 which contains at least one phosphorothioate intersugar linkage.

5. The oligonucleotide of claim 1 which has at least one 2'-O-methoxyethyl modification.

6. The oligonucleotide of claim 1 which contains at least one 5-methyl cytidine.

7. The oligonucleotide of claim 5 in which every 2'-O-methoxyethyl modified cytidine residue is a 5-methylcytidine.

8. An antisense oligonucleotide 8 to 30 nucleotides in length comprising a nucleotide sequence complementary to a nucleic acid molecule encoding human thymidylate synthase, wherein said oligonucleotide is complementary to the 3' untranslated region of said nucleic acid molecule and which inhibits cell proliferation.

9. The oligonucleotide of claim 8 comprising SEQ ID NO: 2, 3, 4, 5, or 6.

10. The oligonucleotide of claim 8 comprising SEQ ID NO: 4, 5, or 6.

* * * * *

United States Patent and Trademark Office
Certificate

Patent No. 6,087,489                                                                      Patented: July 11, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Nicholas M. Dean, Encinitas, CA; James Koropatnick, London, Canada; Mark D. Vincent, London, Canada Signed and Sealed this Eleventh Day of April 2006.

ANDREW WANG
*Supervisory Patent Examiner*
Art Unit 1639